United States Patent
Gorter de Vries et al.

(10) Patent No.: US 11,130,739 B2
(45) Date of Patent: *Sep. 28, 2021

(54) CRYSTALLINE FORMS OF (S)-AFOXOLANER

(71) Applicant: BOEHRINGER INGELHEIM ANIMAL HEALTH USA INC., Duluth, GA (US)

(72) Inventors: Roelof Johannes Gorter de Vries, St. Genis les Ollieres (FR); Bruno Baillon, Le Poet (FR); Sylvaine Lafont, Chateau-Arnoux (FR); Myriam Gay de Saint Michel, Peyruis (FR); Stephane Kozlovic, Sisteron (FR)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/825,616

(22) Filed: Mar. 20, 2020

(65) Prior Publication Data

US 2020/0270219 A1 Aug. 27, 2020

Related U.S. Application Data

(63) Continuation of application No. 15/946,642, filed on Apr. 5, 2018, now Pat. No. 10,662,163.

(60) Provisional application No. 62/482,175, filed on Apr. 5, 2017.

(51) Int. Cl.
*C07D 261/04* (2006.01)

(52) U.S. Cl.
CPC ........ *C07D 261/04* (2013.01); *C07B 2200/13* (2013.01)

(58) Field of Classification Search
CPC .................................................. C07B 2200/13
See application file for complete search history.

(56) References Cited

U.S. PATENT DOCUMENTS

| 7,964,204 B2 | 6/2011 | Lahm et al. |
| 10,662,163 B2 * | 5/2020 | Gorter de Vries ... C07D 261/04 |

FOREIGN PATENT DOCUMENTS

| WO | 2009/002809 A2 | 12/2008 | |
| WO | 2011/149749 A1 | 12/2011 | |
| WO | 2016/138339 A1 | 9/2016 | |
| WO | 2017/176948 A1 | 10/2017 | |
| WO | WO-2017176948 A1 * | 10/2017 | ........... C07D 261/04 |

OTHER PUBLICATIONS

Petropavlov et al: "Crystal growth in organic solids during desolvation", Journal of Crystal Growth, Elsevier, Amsterdam, NL, vol. 52, Apr. 1, 1981 (Apr. 1, 1981), pp. 889-893.
Keith Guillory J Ed—Harry G Brittain (Ed): "Generation of Polymorphs, Hydrates, Solvates, and Amorphous Solids", Dec. 31, 1999 (Dec. 31, 1999), Polymorphism in Pharmaceutical Solids Ed. 2, M. Dekker, USA, pp. 183-226.

* cited by examiner

*Primary Examiner* — John S Kenyon
(74) *Attorney, Agent, or Firm* — John Ezcurra

(57) ABSTRACT

The present invention provides crystalline forms of compound of formula (Ia) and processes of making the crystalline forms. Also provided are compositions comprising the crystalline forms and methods of use of the crystalline forms.

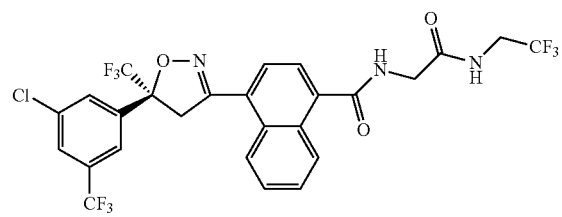

(Ia)

21 Claims, 4 Drawing Sheets

CRYSTALLINE FORMS OF (S)-AFOXOLANER

CROSS-REFERENCE TO RELATED APPLICATIONS

This application claims the benefit of priority to U.S. Provisional Application No. 62/482,175, filed Apr. 5, 2017, which is incorporated herein by reference.

FIELD OF THE INVENTION

The present disclosure generally relates to solid forms of compound of formula (Ia)

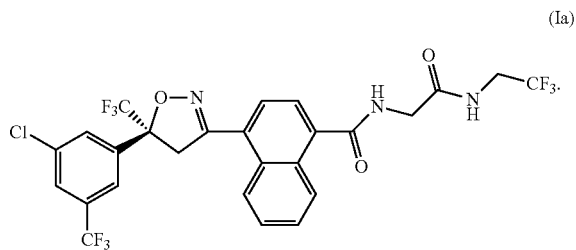 [SMILES: O=C(CNC(=O)c1ccc(C2=NO[C@@](c3cc(Cl)cc(C(F)(F)F)c3)(C(F)(F)F)C2)c2ccccc12)NCC(F)(F)F]

(Ia)

BACKGROUND OF THE INVENTION

Polymorphs can differ in such physical and chemical (i.e. physiochemical) properties as crystal shape, density, hardness, color, chemical stability, melting point, hygroscopicity, suspendability and dissolution rate, and such biological properties as biological availability. Predicting physiochemical properties for a crystal form or crystal forms in which the solid state of a chemical compound can exist remains impossible.

Also, the single enantiomers of pharmacologically active compounds have met an increased interest in the last years because of improved pharmacokinetic and biological properties. Therefore, there is a need for a process that can be used in large scale for the preparation of the single enantiomers of afoxolaner. Generally, asymmetric processes for obtaining chiral molecules afford optically active molecules in enantiomerically enriched forms rather than in pure single enantiomeric forms unless the processes include resolution methods. Therefore, there is also a need for a method that can be used in large scale for the enhancement of enantiomeric purity of optically active (S)-afoxolaner.

Afoxolaner may exist as two enantiomeric configurations, namely the (S)-enantiomer which is the compound of formula (Ia):

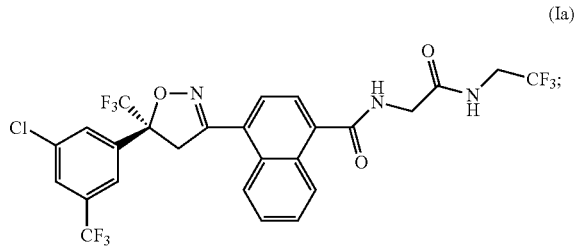 [SMILES: O=C(CNC(=O)c1ccc(C2=NO[C@@](c3cc(Cl)cc(C(F)(F)F)c3)(C(F)(F)F)C2)c2ccccc12)NCC(F)(F)F]

(Ia)

and the (R)-enantiomer, which is a compound of formula (Ib):

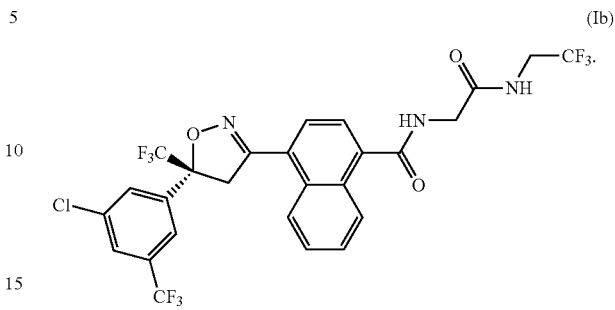

(Ib)

Furthermore, even predicting whether the solid state of a compound may be present in more than one crystal form is not possible.

U.S. Patent Application No. 62/319,207, which is the priority document for U.S. patent application Ser. No. 15/480,316 published as US 2017/0311601 A1 (all incorporated herein by reference) discloses a compound of formula (Ia) and methods for its preparation, as well as the utility of this compound as an invertebrate pest control agent. New solid forms of this compound have now been discovered.

U.S. Pat. No. 8,410,153, incorporated herein by reference, describes afoxolaner as being effective in treating or preventing parasitic infections or infestations in or on animals.

INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention.

SUMMARY OF THE INVENTION

This invention relates to solid forms of compound of formula (Ia). More particularly, this invention is directed to crystalline forms of the compound of formula (Ia) designated Form I and Form II and for processes to prepare these crystalline forms.

This invention also relates to compositions containing solid forms of compound of formula (Ia) and methods for controlling an invertebrate pest comprising contacting the invertebrate pest or its environment with a biologically effective amount of a solid form of compound of formula (Ia) or a composition containing a solid form of compound of formula (Ia).

The invention in its particular features will become more apparent from the following detailed description considered with reference to the accompanying examples. The following description will continue to discuss the problems and solutions offered by the present invention as they pertain to antiparasitic applications.

DETAILED DESCRIPTION OF THE INVENTION

Figure 1:
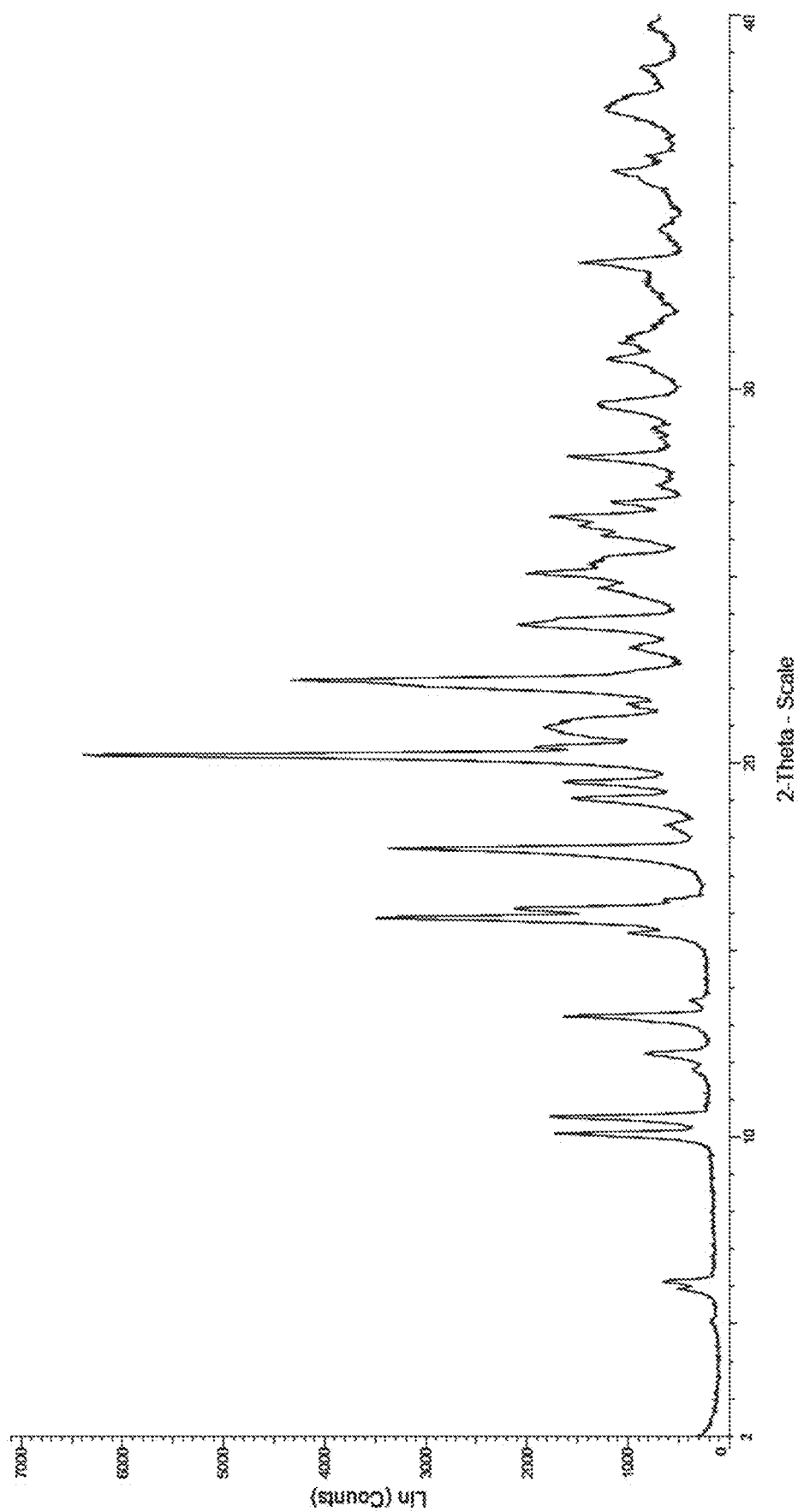
FIG. 1 shows a powder X-ray diffraction pattern of crystalline Form I of compound of formula (Ia) showing absolute intensity count graphed against 2θ reflection positions.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "administering" as used herein refers to any method which, in sound veterinary practice delivers the compound or compositions used in this invention to the subject to be treated in such a manner so as to be effective in the prevention or treatment of a parasitic infestation. For example, the compound or composition is administered via oral, parenteral, percutaneous or topical routes. Topical administration comprises, in particular, skin solutions (pour-on or spot-on), sprays, baths, showers, jets, powders, greases, shampoos, creams, etc. The pour-on type skin solutions may be designed for percutaneous delivery or for distribution of the active on the exterior of the animal.

The term "anhydrate" or "anhydrous polymorph" or "anhydrous crystalline form" refers to a crystalline form that does not have water bound in the crystal lattice. However, the crystals may contain trace amount of water or other solvents not bound in the crystal lattice.

The term "amorphous" as applied to afoxolaner herein refers to a solid state wherein the afoxolaner molecules are present in a disordered arrangement and do not form a distinguishable crystal lattice or unit cell. When subjected to X-ray powder diffraction, amorphous afoxolaner does not produce any characteristic crystalline peaks.

The term "chemical purity" refers to the overall level of a desired product. If a compound is present in enantiomeric forms, "chemical purity" as used herein would include both enantiomeric forms in the calculation of the overall level of the desired product. If a compound is present in solvate forms, "chemical purity" as used herein would include the solvate in the calculation of the overall level of the desired product. Impurities may be in the form of, for example, the presence of unwanted process reagents, process intermediates, degradation products or oxidation products. In particular embodiments the chemical purity is high, that is greater than 90% chemical purity, especially above 92.5%, 95%, 96%, 97%, 98%, 99%, 99.9% and includes 100%. The purity may be measured a variety of techniques, including HPLC analysis.

The term "effective amount" as used herein refers to a sufficient amount of the crystalline form of the compound of formula (Ia) to eradicate or reduce the number of parasites infesting the animal. In some embodiments, an effective amount of the active agent achieves at least 70% efficacy against the target parasite. In other embodiments, an effective amount of the crystal form of the invention achieves at least 80%, or at least 90% efficacy against the target pests. Preferably, an effective amount of the crystal form of the invention will achieve at least 95%, at least 98% or 100% efficacy against the target parasites.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light, to the same degree, in the opposite direction.

The term "enantiomeric excess" or "e.e." as used herein refers to a difference between the amount of one enantiomer and the amount of the other enantiomer that is present in the product mixture. The enantiomeric excess value in each example given below gives an indication of the relative amount of each enantiomer. The value is defined as the difference between the relative percentages for the two enantiomers. Thus, for example, when the percentage of the (S)-enantiomer of the compound of the invention is 97.5% and the percentage for the (R)-enantiomer is 2.5%, the enantiomeric excess for the (S)-enantiomer is 95%.

The terms "enantiomerically pure" or "enantiomeric purity" as used herein is a measure of how much more of one enantiomer there is than the other enantiomer in a mixture of enantiomers. For example, a mixture of 99% (S)-enantiomer and 1% (R)-enantiomer has 99% enantiomeric purity of the (S)-enantiomer. Enantiomerically pure is preferably at least 95% or at least 98% enantiomeric purity, more preferably at least about 99%. In another embodiment enantiomerically is about 99.90% to about 100% enantiomeric purity.

The term "isolated" as used herein, in reference to solid state forms of afoxolaner of the present disclosure corresponds to a solid state form of afoxolaner that is physically separated from the solution in which it is formed.

The term "volume of solvent" as used herein refers to the volume of solvent, expressed in liters at ambient temperature, used in a process to dissolve 1 kg of solid material. For example 5 volumes of solvent used in a process starting with 1 kg of starting material would equal 5 liters of solvent.

As used herein, a "lower alkyl alcohol" refers to a branched or straight-chained $C_1$-$C_6$ alkyl group containing one hydroxy group, such as ethanol, n-propanol, isopropanol, n-butanol, isobutyl alcohol, sec-butyl alcohol, t-butyl alcohol, pentanol, hexanol, etc; with preferred lower alkyl alcohols including ethanol, propanol and isopropanol; most preferably ethanol.

As used herein, an "aliphatic solvent" refers to a linear, branched or cyclic aliphatic solvent containing up to 9 carbon atoms. Aliphatic solvents include alkane, alkene or alkyne solvents. Non-limiting examples of aliphatic solvents include pentane, hexane, heptane, octane, cyclopentane, cyclohexane, and the like.

The term "non-solvate polymorph" or "non-solvate crystalline form" refers to a crystalline form that does not have a solvent bound in the crystal lattice, for example an anhydrous polymorph. However, the crystals may contain trace amount of solvent not bound in the crystal lattice.

The term "or" as used herein, and unless expressly stated to the contrary, refers to an inclusive or and not to an exclusive or. For example, a condition A or B is satisfied by any one of the following: A is true (or present) and B is false (or not present), A is false (or not present) and B is true (or present), and both A and B are true (or present).

The term "pharmaceutically acceptable carrier" as used herein, may include any and all solvents, diluents, or other liquid or solid vehicles, dispersion or suspension aids, surface active agents, isotonic agents, thickening or emulsifying agents, preservatives, solid binders, lubricants and the like, as suited to the particular dosage form desired. Remington's Pharmaceutical Sciences, Eighteenth Edition, E. W. Martin (Mack Publishing Co., Easton, Pa. 1990) discloses various carriers used in formulating pharmaceutical compositions and known techniques for the preparation thereof. Except insofar as any conventional carrier medium is incompatible with the compound (Ia) such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycerin, glycerin esters, glycols; such as propylene glycol or polyethylene glycol; esters such as ethyl oleate and ethyl laurate; agar, buffering agents such as magnesium hydroxide and aluminum hydroxide; alginic acid; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "polymorph", as used herein, refers to the different crystal structures (of solvated or non-solvated forms) in which a compound can crystallize.

The term "racemic" or "racemate", and other like terms refer to generally equimolar proportions of a (S)-afoxolaner and a (R)-afoxolaner.

The term "seed" as used herein can be used as a noun to describe one or more crystals of crystalline afoxolaner (e.g., polymorph Form I). For example, if it is desired to produce crystalline (S)-afoxolaner polymorph Form I, the seed crystals to be used to enhance the crystallization process can be crystals of (S)-afoxolaner polymorph Form I. The term "seed" or "seeding" can also be used as a verb to describe the act of introducing said one or more crystals of a afoxolaner (e.g., polymorph Form I) into an environment (including, but not limited to e.g., a solution, a mixture, a suspension, or a dispersion) thereby resulting in the formation of more of the same crystals of afoxolaner (e.g., polymorph Form I).

The term "solvate", "solvate polymorph" or "solvate crystalline form" refers to a crystalline form that has solvate bound in the crystal lattice.

The phrase "substantially pure crystal form", unless otherwise specified is to be understood as a substance free of other crystal forms, or amorphous form, at amounts detectable with typical analytical methods such as X-ray powder diffraction and/or solid state infrared absorption, i.e. containing less than 10% of other crystal forms. Preferably, there is less than 5%, more preferably less than 2%, and even more preferably less than 1% of any other crystal form, or amorphous form, of the compound present.

When used in reference to a diffractogram, a spectrum or data presented in a graph, the term "substantially similar" means that the subject diffractogram, spectrum or data presented in a graph encompasses all diffractograms, spectra or data presented in graphs that vary within acceptable boundaries of experimentation that are known to a person of skill in the art. Such boundaries of experimentation will vary depending on the type of the subject diffractogram, spectrum or data presented in a graph, but will nevertheless be known to a person of skill in the art.

The term "treating" or "treat" or "treatment" as used herein is intended the application or administration of a compound or composition of the invention to an animal that has a parasitic infestation for the eradication of the parasite or the reduction of the number of the parasites infesting the animal undergoing treatment. It is noted that the compositions of the invention may be used to prevent such a parasitic infestation.

It is further noted that in this disclosure and particularly in the claims or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

As described herein, the compound of formula (Ia) can be a crystalline form that may exist as one or more polymorphs, including solvate forms. In general, polymorphs (alternatively known in the art as polymorph forms, polymorphic forms or crystal forms) differ with respect to their X-ray powder diffraction patterns, spectroscopic, physicochemical and pharmacokinetic properties, as well as their thermodynamic stability. Also, polymorphs may show different physical properties like crystal shape, chemical stability, dissolution rate and bioavailability as known for polymorphs. Accordingly, a particular polymorph may represent the most suitable form for a given application, including, but not limited to, use in particular administration forms such as suspensions, ointments, tablets or capsules, or in the manufacture of a drug form having preferred pharmacokinetic properties.

Depending upon the intended use of the solid state form of (S)-afoxolaner, processing considerations may favor selection of a specific solid state form or a specific combination of such solid state forms. Use of a solvated crystalline form, instead of Form I or Form II in a composition, eliminates a processing step, namely desolvation, for those processes that otherwise would proceed by desolvation of a solvated crystalline form. However, in the pharmaceutical or veterinary fields, certain solvents are not permitted above threshold levels due to toxicity concerns and must be removed in order to be used in products that are administered to humans or animals. Accordingly, the use of certain solvates is not possible in these fields. Furthermore, it is difficult to remove solvents from crystalline forms of a compound where the solvent is part of the crystal lattice. When a non-solvated crystalline solid form of a compound can be produced the desolvation step can be eliminated, resulting in an improved manufacturing process of the compound. For example, if Form I or Form II is directly crystallized from an appropriate solvent without intervening preparation and desolvation of an intermediate solvated crystalline form significant cost savings and more efficient process is achieved. See, for example, E. Shefter and T. Higuchi, have measured the relative rates of dissolution of several crystalline solvated and non-solvated forms of important pharmaceuticals. J. Pharm. Sci., 52 (8). (1963), 781-91. In the case of the compound of formula (Ia) shown below, it was found that crystallization of the compound from common process solvents, including aromatic solvents such as toluene and the like, resulted in isolation of the compound as a solvate and isolation of a non-solvated form of the compound of formula (Ia) was very difficult. However, the solvate could not be directly used in pharmaceutical or veterinary applications without significantly reducing the level of the solvent, which was not commercially feasible. Therefore, the discovery of the non-solvated Form I and Form II of the compound of formula (Ia) represents a significant improvement in the development of effective parasiticidal compositions for treating or preventing parasitic infestations in animals.

In another embodiment of the invention, solvates, including hydrates, have some variability in the exact molar ratio of their components depending on a variety of conditions understood to a person of skill in the art. For example, a molar ratio of components within a solvate provides a person of skill in the art information as to the general relative quantities of the components of the solvate and in many cases the molar ratio may vary by about plus or minus 20% from a stated range. For example, a molar ratio of 1:1 is understood to include the ratio 1:0.8 as well as 1:1.2 as well as all of the individual ratios in between.

The present invention provides crystalline (S)-afoxolaner Form I substantially free of bound organic solvent, and free of bound water, as characterized by X-Ray Powder Diffraction (XRPD) and/or Differential Scanning Calorimetry (DSC) described in Example 3.

The present invention also provides crystalline (S)-afoxolaner Form II substantially free of bound organic solvent, and free of bound water, as characterized by X-Ray Powder Diffraction (XRPD) and/or Differential Scanning Calorimetry (DSC) described in Example 3.

In addition, the present invention provides a process for preparing (S)-afoxolaner Form I and/or (S)-afoxolaner Form II, or a mixture thereof, comprising crystallizing the compound from a solvent mixture comprising an aliphatic solvent and a co-solvent.

Embodiments of the present invention as described in the Summary of the Invention include those described below.

Embodiment (1)

A crystalline compound of formula (Ia), designated as Form I,

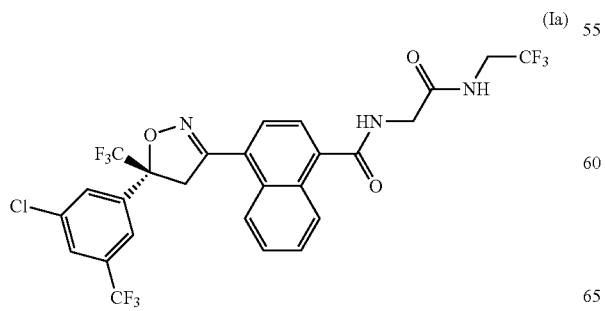

wherein said crystals are characterized by having an x-ray powder diffraction pattern comprising three, four, five, six, seven or more peaks selected from the group consisting of: 10.03°, 10.48°, 13.16°, 15.42°, 15.80°, 16.07°, 17.65°, 20.16°, 22.15°, 23.68°, 26.52°, and 28.13° 2θ±0.2 as determined on a diffractometer using Cu-Kα radiation.

Embodiment 2

The crystalline compound of formula (Ia) according to Embodiment (1), characterized by having an x-ray powder diffraction pattern comprising three or more peaks selected from the group consisting of: 10.03°, 10.48°, 13.16°, 20.16°, and 22.15° 2θ±0.2 as determined on a diffractometer using Cu-Kα radiation.

Embodiment 3

The crystalline compound of formula (Ia) according to Embodiment (1), characterized by having an x-ray powder diffraction pattern substantially similar to FIG. 1.

Embodiment 4

The crystalline compound of formula (Ia) according to any one of Embodiments (1) to (3), characterized by having a differential scanning calorimetry (DSC) thermogram having an peak at a temperature of about 146° C., and an onset at about 143° C., measured with the heating rate of 5° C./min.

Embodiment 5

The crystalline compound of formula (Ia) according to any one of Embodiments (1) to (4), characterized by having a differential scanning calorimetry (DSC) thermogram having a heat of fusion of about 61.7 J/g.

Embodiment 6

Figure 2:
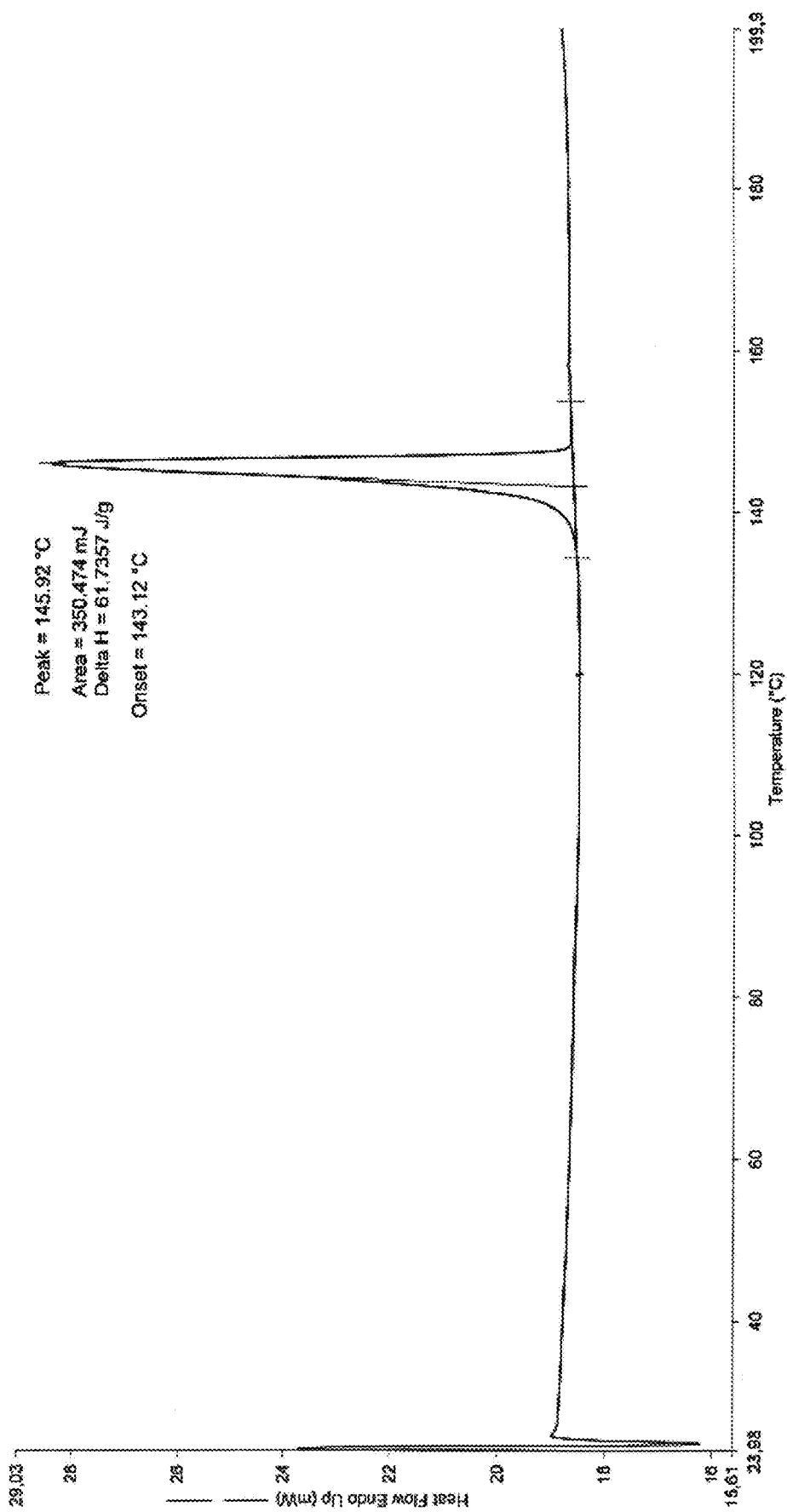
FIG. 2 shows a differential scanning calorimetry thermogram of crystalline Form I of compound of formula (Ia).

The crystalline compound of formula (Ia) according to any one of Embodiments (1) to (5), characterized by having a differential scanning calorimetry thermogram substantially similar to FIG. 2.

Embodiment 7

The crystalline compound of formula (Ia) according to any one of Embodiments (1) to (6), wherein the crystalline form is isolated.

Embodiment 8

The crystalline compound of formula (Ia) according to any one of Embodiments (1) to (7), wherein the crystalline form is non-solvated.

Embodiment 9

The crystalline compound of formula (Ia) according to any one of Embodiments (1) to (8), which is enantiomerically pure.

Embodiment 10

The crystalline compound of formula (Ia) according to any one of Embodiments (1) to (9), having a degree of chemical purity of at least about 95%.

Embodiment 11

The crystalline compound of formula (Ia) according to any one of Embodiments (1) to (10), having a degree of chemical purity of at least about 98%.

Embodiment 12

The crystalline compound of formula (Ia) according to any one of Embodiments (1) to (10), having a degree of chemical purity of at least about 99%.

Embodiment 13

The crystalline compound of formula (Ia) according to any one of Embodiments (1) to (12), having a degree of chemical purity in the range of about 98.00% to about 99.00%.

Embodiment 14

The crystalline compound of formula (Ia) according to any one of Embodiments (1) to (13), having a degree of chemical purity in the range of about 99.00% to about 99.95%.

Embodiment 15

The crystalline compound of formula (Ia) according to any one of Embodiments (1) to (13), having a degree of chemical purity in the range of about 99.00% to about 100%.

Embodiment 16

The crystalline compound of formula (Ia) according to any one of Embodiments (1) to (15), having a degree of chemical purity of about 99.90%.

Embodiment 17

The crystalline compound of formula (Ia) according to any one of Embodiments (1) to (16), having an enantiomeric purity in the range of about 98.0 to about 99.0%.

Embodiment 18

The crystalline compound of formula (Ia) according to any one of Embodiments (1) to (17), having an enantiomeric purity in the range of about 99.0 to about 100%.

Embodiment 19

The crystalline compound of formula (Ia) according to any one of Embodiments (1) to (18), having a degree of chemical purity in the range of about 99.00% to about 99.95% and an enantiomeric purity in the range of about 99.0 to about 100%.

Embodiment 20

The crystalline compound of formula (Ia) according to any one of Embodiments (1) to (19), having a degree of chemical purity of about 99.90% and an enantiomeric purity of about 99.90%.

Embodiment 21

The crystalline compound of formula (Ia) according to any one of Embodiments (1) to (20), in substantially pure crystal form.

Embodiment 22

A crystal form of (S)-afoxolaner which is bioequivalent to the crystalline compound of formula (Ia) according to any one of Embodiments (1) to (21).

Embodiment 23

A pharmaceutical composition comprising the crystalline compound of formula (Ia) according to any one of Embodiments (1) to (22), and at least one pharmaceutically acceptable excipient.

Embodiment 24

A composition comprising the crystalline compound of formula (Ia) according to any one of Embodiments (1) to (22), wherein said crystalline compound of formula (Ia) is in admixture with one or more distinct polymorphic forms of, or an amorphous compound of, formula (Ia).

Embodiment 25

The composition according to Embodiment (24), wherein said distinct polymorphic form is Form II.

Embodiment 26

The composition according to Embodiment (24), wherein said crystalline compound of formula (Ia) is in admixture with an amorphous compound of formula (Ia).

Embodiment 27

The pharmaceutical composition according to any one of Embodiments (23) to (26), wherein the composition comprises at least about 50.0% by weight of the crystalline compound of formula (Ia) according to embodiment 1, based on the total weight of compound of formula (Ia) in the composition.

Embodiment 28

The pharmaceutical composition according to any one of Embodiments (23) to (27), wherein the composition comprises at least about 70% by weight of the crystalline compound of formula (Ia) according to embodiment 1, based on the total weight of compound of formula (Ia) in the composition.

Embodiment 29

The pharmaceutical composition according to any one of Embodiments (23) to (28), wherein the composition comprises at least about 80% by weight of the crystalline compound of formula (Ia) according to embodiment 1, based on the total weight of compound of formula (Ia) in the composition.

Embodiment 30

The pharmaceutical composition according to any one of Embodiments (23) to (29), wherein the composition comprises at least about 90% by weight of the crystalline compound of formula (Ia) according to embodiment 1, based on the total weight of compound of formula (Ia) in the composition.

Embodiment 31

The pharmaceutical composition according to any one of Embodiments (23) to (28), wherein the composition comprises at least about 95% by weight of the crystalline compound of formula (Ia) according to embodiment 1, based on the total weight of compound of formula (Ia) in the composition.

Embodiment 32

The pharmaceutical composition according to any one of Embodiments (23) to (31), wherein the composition comprises at least about 99.0% by weight of crystalline compound of formula (Ia) according to embodiment 1, based on the total weight of compound of formula (Ia) in the composition.

Embodiment 33

A process for preparing a crystalline compound of formula (Ia) according to any one of Embodiments (1) to (22), which comprises:—
(a) heating a mixture of a toluene solvate of (S)-afoxolaner in a solvent, wherein the solvent is acetonitrile, ethyl acetate, a linear, branched or cyclic aliphatic solvent (e.g. pentane, hexane, heptane, octane, cyclopentane, cyclohexane and the like) or an alcohol, or a combination thereof, until dissolution has occurred;
(b) optionally adding a co-solvent;
(c) reducing the temperature of the solvent system to induce nucleation;
(d) maintaining the mixture at a temperature below that at which nucleation has commenced; and
(e) isolating the crystalline compound of formula (Ia) so deposited.

Embodiment 34

The process according to Embodiment (33), wherein the co-solvent is isobutyl ketone or acetone.

Embodiment 35

The process according to Embodiment (33), wherein the aliphatic solvent is a $C_1$-$C_8$ linear, branched or cyclic alkane solvent Embodiment 36

The process according to according to any one of Embodiments (33) to (35), wherein the alcohol is a lower alkyl alcohol.

Embodiment 37

The process according to according to any one of Embodiments (33) to (36), wherein the alcohol is ethanol.

Embodiment 38

The process according to any one of Embodiments (33) to (37), wherein the solvent is a mixture comprising ethanol and cyclohexane.

Embodiment 39

The process according to Embodiment (38), wherein the mixture of ethanol and cyclohexane is about 10:90 to about 99:1 (v/v) ethanol to cyclohexane.

Embodiment 40

The process according to Embodiment (38), wherein the mixture of ethanol and cyclohexane is about 1:99 to about 25:75 (v/v) ethanol to cyclohexane.

Embodiment 41

The process according to Embodiment (38), wherein the mixture of ethanol and cyclohexane is about 3:97 to about 10:90 (v/v) ethanol to cyclohexane.

Embodiment 42

The process of according to Embodiment (38) wherein the mixture of ethanol and cyclohexane is about 5:95 to about 10:90 (v/v) ethanol to cyclohexane.

Embodiment 43

The process of according to Embodiment (38) wherein the mixture of ethanol and cyclohexane is about 8:92 (v/v) ethanol to cyclohexane.

Embodiment 44

The process according to any one of Embodiments (33) to (43), comprising seeding with enantiomerically pure (S)-afoxolaner Form I.

Embodiment 45

The process according to any one of Embodiments (33) to (44), wherein the heating is to about 50 to about 80 degrees Celsius.

Embodiment 46

The process according to any one of Embodiments (33) to (45), wherein reducing the temperature is to a temperature of about 10 degrees Celsius or lower.

Embodiment 47

The process according to any one of Embodiments (33) to (46), wherein reducing the temperature is to a temperature of about 5 degree Celsius or lower.

Embodiment 48

The process according to any one of Embodiments (33) to (47), wherein reducing the temperature is at a rate of about 3 degrees Celsius/hour.

Embodiment 49

A process for preparing a crystalline Form I of (S)-afoxolaner of embodiment 1 which comprises:—
(a) heating a mixture of the toluene solvate of (S)-afoxolaner having an enantiomeric purity ≥97% in a solvent, wherein the solvent is acetonitrile, ethyl acetate, a linear, branched or cyclic alkane solvent or an alcohol, or a combination thereof, until dissolution has occurred;
(b) optionally adding a co-solvent;
(c) reducing the temperature of the solvent system to induce nucleation;
(d) maintaining the mixture at a temperature below that at which nucleation has commenced; and
(e) isolating the crystalline Form I of (S)-afoxolaner so deposited.

Embodiment 50

A process according to according to any one of Embodiments (33) to (49), in which the crystalline compound of formula (Ia) isolated is enantiomerically enriched with (S)-afoxolaner.

Embodiment 51

A crystalline form of (S)-afoxolaner produced by the process according to any one of Embodiments (33) to (50).

Embodiment 52

A crystalline form of (S)-afoxolaner as disclosed in any of the examples.

Embodiment 53

A method of treating or preventing parasitic infection or infestation in an animal comprising administering to the animal an effective amount of a crystalline form of (S)-afoxolaner of any one of Embodiments (1) to (22) or Embodiment (52) or a composition of any one of Embodiments 23-32.

Embodiment 54

A crystalline compound of formula (Ia), designated as Form II,

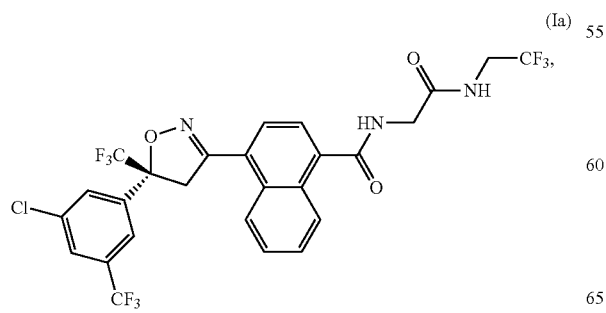

wherein said crystals are characterized by having an x-ray powder diffraction pattern comprising three, four, five, six, seven or more peaks selected from the group consisting of: 5.99°, 12.99°, 15.80°, 18.71°, 19.33°, 20.24°, 21.65°, 22.17°, 26.11° and 29.00° 2θ±0.2 as determined on a diffractometer using Cu-Kα radiation.

Embodiment 55

The crystalline compound of formula (Ia) according Embodiment (54), wherein said crystals are characterized by having an x-ray powder diffraction pattern comprising three or more peaks selected from the group consisting of: 5.99°, 12.99°, 15.80°, 22.17°, 26.110 2θ±0.2 as determined on a diffractometer using Cu-Kα radiation.

Embodiment 56

Figure 3:
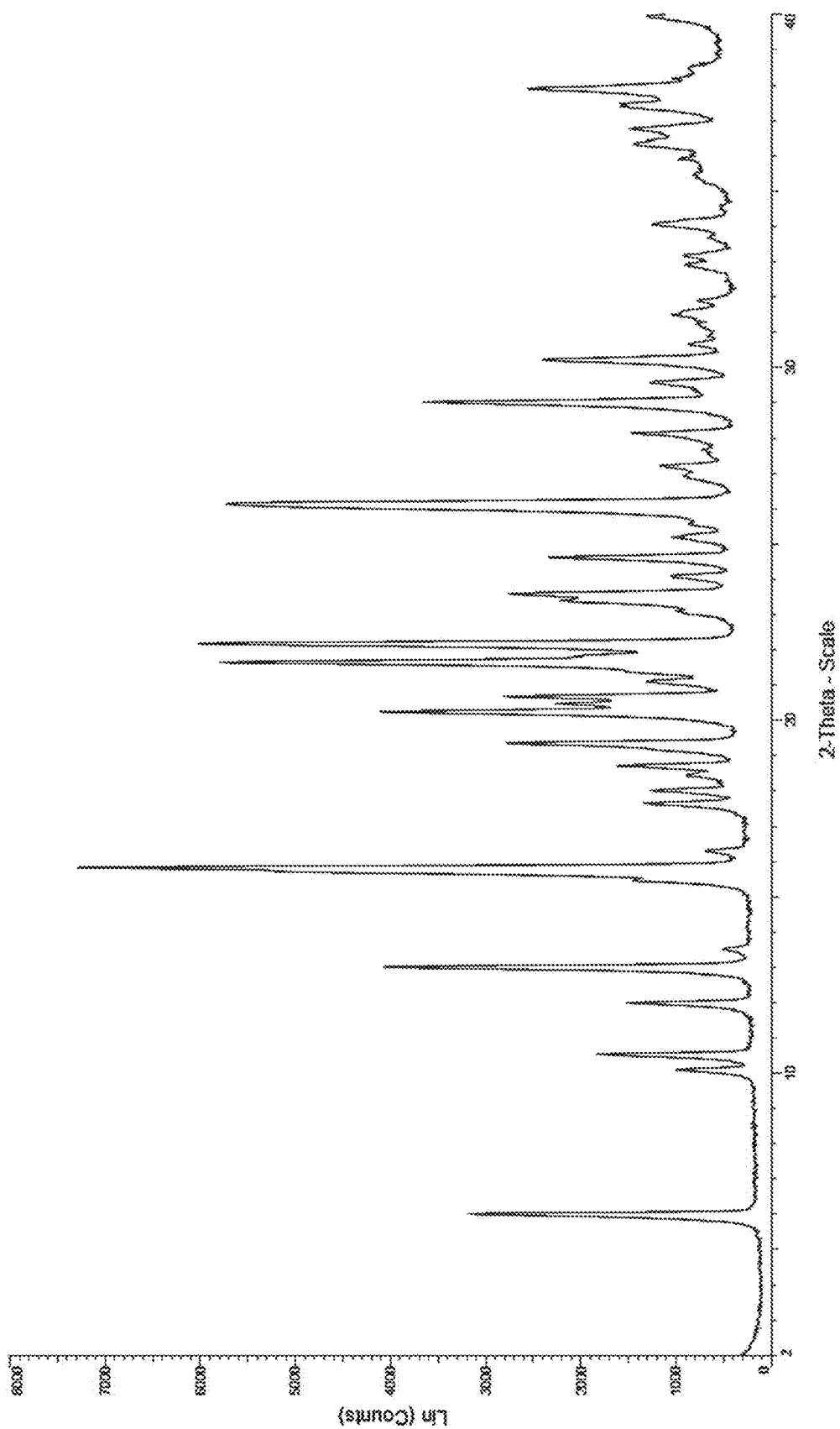
FIG. 3 shows a powder X-ray diffraction pattern of crystalline Form II of compound of formula (Ia) showing absolute intensity count graphed against 2θ reflection positions.

The crystalline compound of formula (Ia) according to any one of Embodiments (54) or (55), characterized by having an x-ray powder diffraction pattern substantially similar to FIG. 3.

Embodiment 57

The crystalline compound of formula (Ia) according to any one of Embodiments (54) to (56), characterized by having a differential scanning calorimetry (DSC) thermogram having an peak at a temperature of about 149° C., and an onset at about 146° C., measured with the heating rate of 5° C./min.

Embodiment 58

The crystalline compound of formula (Ia) according to any one of Embodiments (54) to (57), characterized by having a differential scanning calorimetry (DSC) thermogram having a heat of fusion about 65.7 J/g.

Embodiment 59

Figure 4:
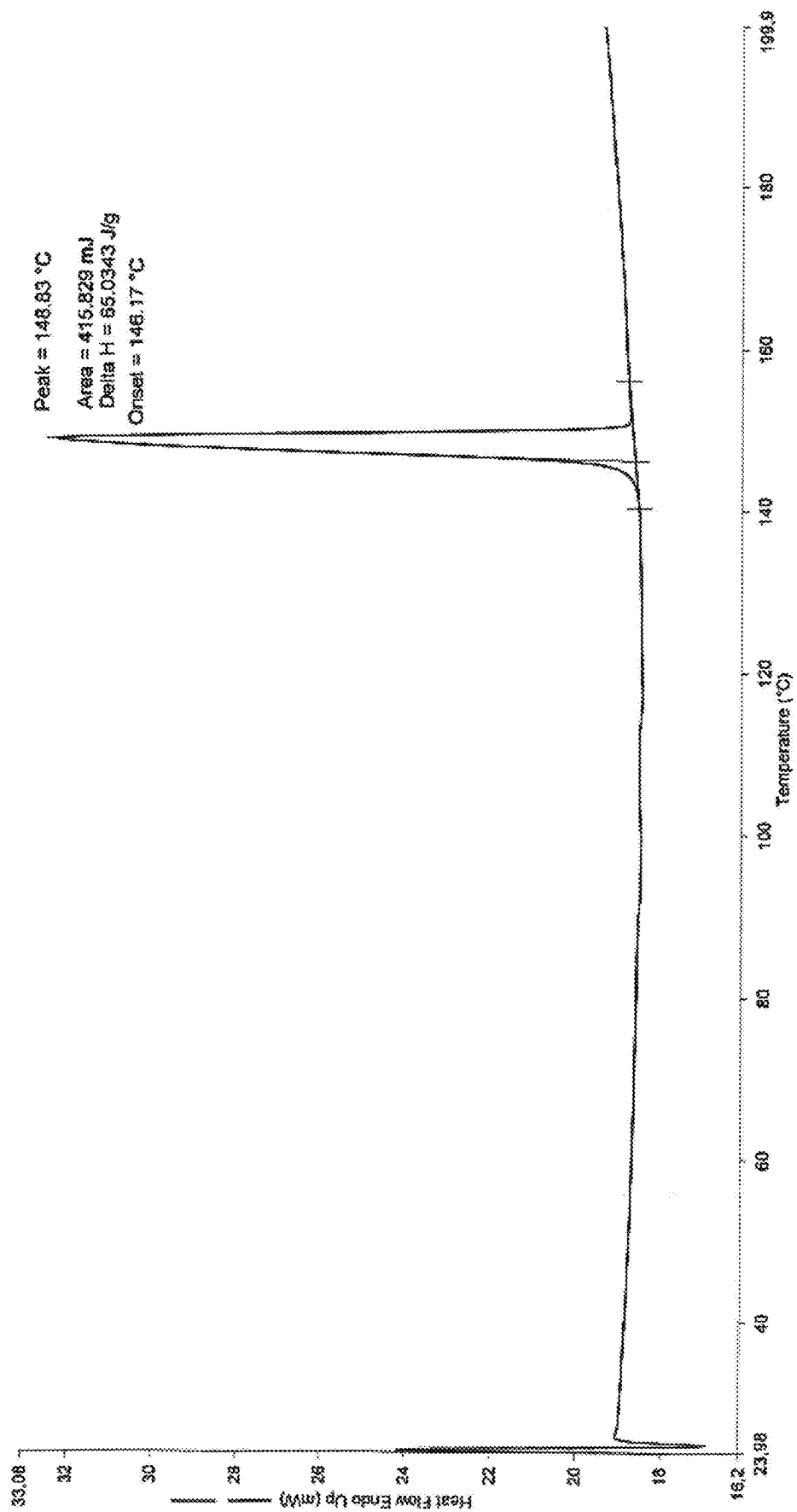
FIG. 4 shows a differential scanning calorimetry thermogram of crystalline Form II of compound of formula (Ia).

The crystalline compound of formula (Ia) according to any one of Embodiments (54) to (58), characterized by having a differential scanning calorimetry thermogram substantially similar to FIG. 4.

Embodiment 60

The crystalline compound of formula (Ia) according to any one of Embodiments (54) to (59), wherein the crystalline form is isolated.

Embodiment 61

The crystalline compound of formula (Ia) according to any one of Embodiments (54) to (60), wherein the crystalline form is non-solvated.

Embodiment 62

The crystalline compound of formula (Ia) according to any one of Embodiments (54) to (61), which is enantiomerically pure.

Embodiment 63

The crystalline compound of formula (Ia) according to any one of Embodiments (54) to (62), having a degree of chemical purity of at least about 95%.

Embodiment 64

The crystalline compound of formula (Ia) according to any one of Embodiments (54) to (63), having a degree of chemical purity of at least about 98%.

Embodiment 65

The crystalline compound of formula (Ia) according to any one of Embodiments (54) to (64), having a degree of chemical purity of at least about 99%.

Embodiment 66

The crystalline compound of formula (Ia) according to any one of Embodiments (54) to (65), having a degree of chemical purity in the range of about 98.00% to about 99.00%.

Embodiment 67

The crystalline compound of formula (Ia) according to any one of Embodiments (54) to (66), having a degree of chemical purity in the range of about 99.00% to about 99.95%.

Embodiment 68

The crystalline compound of formula (Ia) according to any one of Embodiments (54) to (67), having a degree of chemical purity in the range of about 99.00% to about 100%.

Embodiment 69

The crystalline compound of formula (Ia) according to any one of Embodiments (54) to (68), having a degree of chemical purity of about 99.90%.

Embodiment 70

The crystalline compound of formula (Ia) according to any one of Embodiments (54) to (69), having an enantiomeric purity in the range of about 98.0 to about 99.0%.

Embodiment 71

The crystalline compound of formula (Ia) according to any one of Embodiments (54) to (70), having an enantiomeric purity in the range of about 99.0 to about 100%.

Embodiment 72

The crystalline compound of formula (Ia) according to any one of Embodiments (54) to (70), having a degree of chemical purity in the range of about 99.00% to about 99.95% and an enantiomeric purity in the range of about 99.0 to about 100%.

Embodiment 73

The crystalline compound of formula (Ia) according to any one of Embodiments (54) to (72), having a degree of chemical purity of about 99.90% and an optical purity of about 99.90%.

Embodiment 74

The crystalline compound of formula (Ia) according to any one of Embodiments (54) to (73), in substantially pure crystal form.

Embodiment 75

A crystal form of (S)-afoxolaner which is bioequivalent to the crystalline compound of formula (Ia) according to any one of Embodiments (54) to (74).

Embodiment 76

A pharmaceutical composition comprising the crystalline compound of formula (Ia) according to any one of Embodiments (54) to (75), and at least one pharmaceutically acceptable excipient.

Embodiment 77

A composition comprising the crystalline compound of formula (Ia) according to Embodiment (76), wherein said crystalline compound of formula (Ia) is in admixture with one or more distinct polymorphic forms of, or an amorphous compound of, formula (Ia).

Embodiment 78

The composition according to Embodiment (77), wherein said distinct polymorphic form is Form I.

Embodiment 79

The composition according to Embodiment (77), wherein said crystalline compound of formula (Ia) is in admixture with an amorphous compound of formula (Ia).

Embodiment 80

The pharmaceutical composition according to any one of Embodiments (76) to (79), wherein the composition comprises at least 50.0% by weight of the crystalline compound of formula (Ia) according to embodiment 53, based on the total weight of compound of formula (Ia) in the composition.

Embodiment 81

The pharmaceutical composition according to any one of Embodiments (76) to (80), wherein the composition comprises at least about 70% by weight of the crystalline compound of formula (Ia) according to embodiment 53, based on the total weight of compound of formula (Ia) in the composition.

Embodiment 82

The pharmaceutical composition according to any one of Embodiments (76) to (81), wherein the composition comprises at least about 80% by weight of the crystalline compound of formula (Ia) according to embodiment 53, based on the total weight of compound of formula (Ia) in the composition.

Embodiment 83

The pharmaceutical composition according to any one of Embodiments (76) to (80), wherein the composition comprises at least about 90% by weight of the crystalline compound of formula (Ia) according to embodiment 53, based on the total weight of compound of formula (Ia) in the composition.

Embodiment 84

The pharmaceutical composition according to any one of Embodiments (76) to (83), wherein the composition comprises at least about 95% by weight of the crystalline compound of formula (Ia) according to embodiment 53, based on the total weight of compound of formula (Ia) in the composition.

Embodiment 85

The pharmaceutical composition according to any one of Embodiments (76) to (84), wherein the composition comprises at least 99.0% by weight of crystalline compound of formula (Ia) according to embodiment 53, based on the total weight of compound of formula (Ia) in the composition.

Embodiment 86

A process for preparing a crystalline compound of formula (Ia) according to Embodiment (54), which comprises:—
(a) heating a mixture of the toluene solvate of (S)-afoxolaner in a solvent, wherein the solvent is acetonitrile, ethyl acetate, a linear, branched or cyclic aliphatic solvent (e.g. pentane, hexane, heptane, octane, cyclopentane, cyclohexane and the like) or an alcohol, or a mixture thereof, until dissolution has occurred;
(b) optionally adding a co-solvent;
(c) reducing the temperature of the solvent system to induce nucleation;
(d) maintaining the mixture at a temperature below that at which nucleation has commenced; and
(e) isolating the crystalline compound of formula (Ia) so deposited.

Embodiment 87

The process according to Embodiment (86), wherein the co-solvent is isobutyl ketone or acetone.

Embodiment 88

The process according to any one of Embodiments (86) to (87), wherein the alcohol is ethanol.

Embodiment 89

The process according to any one of Embodiments (86) to (88), wherein the solvent is a mixture comprising ethanol and cyclohexane.

Embodiment 90

The process of embodiment 89 wherein the mixture of ethanol and cyclohexane is about 15:85 to about 99:1 (v/v) ethanol to cyclohexane.

Embodiment 91

The process according to Embodiment (89), wherein the mixture of ethanol and cyclohexane is about 1:99 to about 25:75 (v/v) ethanol to cyclohexane.

Embodiment 92

The process according to Embodiment (89), wherein the mixture of ethanol and cyclohexane is about 3:97 to about 10:90 (v/v) ethanol to cyclohexane.

Embodiment 93

The process of according to Embodiment (89) wherein the mixture of ethanol and cyclohexane is about 5:95 to about 10:90 (v/v) ethanol to cyclohexane.

Embodiment 94

The process according to any one of Embodiments (89) to (91), wherein the mixture of ethanol and cyclohexane is about 15:85 (v/v) ethanol to cyclohexane.

Embodiment 95

The process according to any one of Embodiments (86) to (94), comprising seeding with enantiomerically pure (S)-afoxolaner Form II.

Embodiment 96

The process according to any one of Embodiments (86) to (95), wherein the heating is to about 50 to about 80 degrees Celsius.

Embodiment 97

The process according to any one of Embodiments (86) to (96), wherein reducing the temperature is to a temperature of about 10 degrees Celsius or lower.

Embodiment 98

The process according to any one of Embodiments (86) to (97), wherein reducing the temperature is to a temperature of about 5 degree Celsius or below.

Embodiment (99)

The process according to any one of Embodiments (86) to (98), wherein reducing the temperature is at a rate of about 3 degrees Celsius/hour.

Embodiment 100

A process for preparing a crystalline Form II of (S)-afoxolaner according to Embodiment (54), which comprises:—
(a) heating a mixture of the toluene solvate of (S)-afoxolaner having an enantiomeric purity of about 97% to about 100% in a solvent, wherein the solvent is acetonitrile, ethyl acetate, a linear, branched or cyclic alkane or an alcohol, or a mixture thereof, until dissolution has occurred;

(b) optionally adding a co-solvent;

(c) reducing the temperature of the solvent system to induce nucleation;

(d) maintaining the mixture at a temperature below that at which nucleation has commenced; and (e) isolating the crystalline Form II of (S)-afoxolaner so deposited.

Embodiment 101

A crystalline form of (S)-afoxolaner produced by the process according to any one of Embodiments (86) to (100).

Embodiment 102

A method of treating or preventing parasitic infection or infestation in an animal comprising administering to the animal an effective amount of a crystalline form of formula (Ia) according to any one of Embodiments (54) to (75) or a composition according to Embodiments 76 to 85.

In another embodiment, the invention provides a crystalline (S)-afoxolaner Form I that exhibits one or more of the characteristic peaks expressed in degrees 2-theta (2θ)±0.2 shown in Table 1 below.

In another embodiment, the invention provides a crystalline (S)-afoxolaner Form I that exhibits at least seven of the characteristic peaks expressed in degrees 2-theta (2θ)±0.2 at one or more of the positions shown in Table 1 below.

In another embodiment, the invention provides a crystalline (S)-afoxolaner Form I that exhibits an endotherm as described in the Examples and shown in FIG. 2.

In another embodiment, the invention provides a crystalline (S)-afoxolaner Form I in combination with crystalline (S)-afoxolaner Form II and/or amorphous (S)-afoxolaner. In another embodiment, the invention provides pesticidal or parasiticidal compositions comprising a crystalline (S)-afoxolaner Form I alone, or in combination with one or more additional active agents, and agriculturally or pharmaceutically acceptable carriers or diluents, wherein at least 80% of the solid form of (S)-afoxolaner is a crystalline Form I.

In one embodiment, the invention provides a crystalline (S)-afoxolaner Form II that exhibits one or more of the characteristic peaks expressed in degrees 2-theta (2θ)±0.2 shown in Table 1 below.

In another embodiment, the invention provides a crystalline (S)-afoxolaner Form II that exhibits at least seven of the characteristic peaks expressed in degrees 2-theta (2θ)+0.2 at one or more of the positions shown in Table 1 below.

In another embodiment, the invention provides a crystalline (S)-afoxolaner Form II that exhibits an endotherm as described in the Examples and shown in FIG. 4.

In another embodiment, the invention provides a crystalline (S)-afoxolaner Form II in combination with crystalline (S)-afoxolaner Form I and/or amorphous (S)-afoxolaner. In another embodiment, the invention provides pesticidal or parasiticidal compositions comprising a crystalline (S)-afoxolaner Form II alone, or in combination with one or more additional active agents, and agriculturally or pharmaceutically acceptable carriers or diluents, wherein at least 80% of the solid form of (S)-afoxolaner is a crystalline Form II.

In other embodiments, the polymorph may contain impurities. Non-limiting examples of impurities residual organic and inorganic molecules such as solvents, water or salts. In one embodiment, the polymorph contains less than 10% by weight total impurities.

In another embodiment, the polymorph contains less than 5%, less than 4%, less than 3%, less than 2%, by weight total impurities. In another embodiment, the polymorph contains less than 1% by weight total impurities. In still another embodiment, the polymorph is substantially free from impurities.

In another embodiment, the invention provides a crystalline (S)-afoxolaner Form I, wherein at least 90% of the solid form is a crystalline Form I form.

In another embodiment, the invention provides a crystalline (S)-afoxolaner, wherein at least 80% of the solid form is a crystalline toluene solvate form.

In another embodiment, the invention provides a crystalline (S)-afoxolaner Form II, wherein at least 90% of the solid form is a crystalline Form II form.

In a particular embodiment, polymorph Form I is in a substantially pure crystal form. In another embodiment, polymorph Form I has less than 10% of other crystal forms. Preferably, there is less than 5%, more preferably less than 2%, and even more preferably less than 1% of any other crystal form, or amorphous form, of the compound present.

Similarly, in a particular embodiment, polymorph Form II is in a substantially pure crystal form. In another embodiment, polymorph Form II has less than 10% of other crystal forms. Preferably, there is less than 5%, more preferably less than 2%, and even more preferably less than 1% of any other crystal form, or amorphous form, of the compound present.

In one embodiment, crystalline Form I and/or Form II of (S)-afoxolaner may be prepared by crystallizing (S)-afoxolaner from a combination of a lower alcohol solvent and an aliphatic solvent according to known methods in the art. In another embodiment, Form I and/or Form II of (S)-afoxolaner may be prepared by crystallizing the compound from an alkyl ester solvent or a solvent mixture containing an alkyl ester solvent. Alkyl ester solvents include, but not limited to, an alkyl acetate solvent such as ethyl acetate, isopropyl acetate, methyl acetate, and the like. In yet another embodiment, Form I and/or Form II of (S)-afoxolaner may be prepared by crystallizing the compound from a nitrile solvent or a solvent mixture containing a nitrile solvent. Nitrile solvents include, but are not limited to acetonitrile. In another embodiment, Form I and/or Form II of (S)-afoxolaner may be prepared by crystallizing the compound from a combination of an aliphatic solvent and an alkylester solvent. In yet another embodiment, Form I and/or Form II (S)-afoxolaner may be prepared by crystallizing the compound from a nitrile solvent including acetonitrile.

In another embodiment, the crystalline (S)-afoxolaner Form I and/or (S)-afoxolaner Form II may be crystallized from water, ethanol, isopropanol, methanol, toluene, dichloromethane, hexane, cyclohexane, diisopropylether or chlorobutane, or a mixture thereof.

Aliphatic solvents are straight, branched, cyclic, primary, secondary or tertiary hydrocarbons and include, but are not limited to, pentane, hexanes, heptane, octane, cyclopentane, cyclohexane, and the like. In another embodiment, crystalline (S)-afoxolaner Form I and/or Form II may be prepared by crystallizing (S)-afoxolaner from a solvent combination of a lower alcohol solvent and a cycloalkyl solvent. In another embodiment, crystalline (S)-afoxolaner Form I and/or Form II may be prepared by crystallizing (S)-afoxolaner from a solvent combination of an alkylester solvent and an aliphatic solvent. In yet another embodiment, crystalline (S)-afoxolaner Form I and/or Form II may be prepared by crystallizing (S)-afoxolaner from a solvent combination of a nitrile solvent and an aliphatic solvent.

In one embodiment of the process, the ratio of the lower alcohol solvent to the aliphatic solvent is about between 1:99 (v/v) to about 25:75 (v/v), lower alcohol to aliphatic solvent. In another embodiment, the ratio of lower alcohol solvent to aliphatic solvent is about 2:98 (v/v) to about 20:80 (v/v). In still another embodiment, the ratio of lower alcohol solvent to aliphatic solvent is about 4:96 to about 15:85. In another embodiment, the ratio of lower alcohol solvent to aliphatic solvent is about 5:95 to about 10:90. In one embodiment, the ratio of lower alcohol solvent to aliphatic solvent is about 6:94 (v/v). In another embodiment, the ratio of lower alcohol solvent to aliphatic solvent is about 7:93 (v/v). In another embodiment, the ratio of lower alcohol solvent to aliphatic solvent is about 8:92 (v/v).

The total volume of solvent may be varied in the process. However, using too much solvent may impact the yield of the process. In contrast, using too little solvent may result in a lower quality product as co-crystallization of an alternate solid form or impurities is more likely. In one embodiment about 7 volumes to about 30 volumes of total solvent or a mixture of solvents may be used. In another embodiment, about 10 volumes to about 25 volumes of total solvent or solvent mixture may be used in the crystallization. In another embodiment about 12 volumes to about 20 volumes of solvent or solvent mixture may be used. In other embodiments, about 12 volumes to 18 volumes, about 13 volumes to about 17 volumes or about 14 volumes to about 16 volumes may be used. In one embodiment, about 15 volumes of total solvent or solvent mixture may be used to crystallize Form I or Form II (S)-afoxolaner.

The source of (S)-afoxolaner may be amorphous (S)-afoxolaner or other solid forms of the compound. Alternatively, a solution of (S)-afoxolaner in another solvent may be used. In one embodiment, the enantiomeric purity of (S)-afoxolaner used in the process is at least about 90% (e.g. ratio of 90:10, (S)-enantiomer to (R)-enantiomer). In another embodiment, the enantiomeric purity of the (S)-afoxolaner is at least about 95%. Preferably, the enantiomeric purity of (S)-afoxolaner used in the process is at least about 98%. In one embodiment, (S)-afoxolaner is dissolved in a suitable solvent at a concentration in which the mixture is a suspension at ambient temperature or below and a solution at elevated temperature and then cooled slowly to induce crystallization from the solvent. In another embodiment, (S)-afoxolaner is dissolved in a solvent in which it is reasonably soluble and then a second solvent in which the compound is not very soluble is added slowly to induce crystallization.

Optionally, a seed can be added to aid crystallization. The seed should be enriched in the desired enantiomer to direct the crystallization to that enantiomer. The enantiomeric excess of the seed can be the same as or different to that of the afoxolaner solution to which it is added, but preferably it is of high enantiomeric excess, eg, at least 90% ee, or higher. Similarly, the seed can be the desired racemic compound to direct the crystallization to that racemic compound.

In an embodiment of the invention, seed crystals may be added to induce crystallization of the (S)-afoxolaner. The amount of seed crystals of (S)-afoxolaner added is such that it exceeds the saturation amount in the solvent being used so that there are undissolved seed crystals present in the solution. A person of skill in the art will understand that the seeding temperature will depend on the solvent used, and if a solvent mixture is used, on the ratio of solvents. In one embodiment, wherein a solvent mixture comprising an aliphatic solvent and a lower alcohol solvent is used, seeding may be done at a temperature range of about 50° C. to about 60° C. In another embodiment, seeding may be conducted at a temperature of about 52° C. to about 58° C. In yet another embodiment, seeding may be done at a temperature of about 53° C. to 57° C. In yet another embodiment, seeding may be done at 55° C.

The mixture is allowed to stand at a temperature of from about 10*C to about 65° C., preferably about 10° C. to about 60° C. or about 10° C. to about 30° C. In one embodiment, the mixture after seeding is aged at a temperature of about 25° C. to about 45° C. and aged and then heated to a temperature of about 50° C. to about 60° C. and aged again before cooling further to isolate the crystallized product. This this cycle may be repeated. The heating/cooling cycle may be used to increase the size of the crystals formed; however, this process is not absolutely necessary. In one embodiment, the mixture is allowed to age at the desired temperature for at least about 15 minutes. In other embodiments, the mixture is allowed to age at least about 30 minutes or at least about 1 hour. In other embodiments, the mixture is allowed to age at the desired temperature at least about 2 hours, at least about 3 hours, or longer. The length of the age time may affect the yield of the process if the aging time is not sufficient to achieve equilibrium solubility at the aging temperature; however, as long as the mixture is stable the length of the aging step is not critical and the mixture may be kept for a longer period of time at the aging temperature. In one embodiment, the mixture is aged at the desired temperature from about 2 hours to about 27 hours. The crystallized mixture is then cooled further to a temperature of below about 20° C. and aged prior to isolation of the crystals by filtration or centrifugation. In one embodiment, the mixture is cooled to a temperature of about 0° C. to about 20° C. In another embodiment, the mixture is cooled to a temperature of about 0° C. to about 15° C. or about 5° C. to about 20° C. In yet another embodiment, the mixture is cooled to a temperature of about 5° C. to about 15° C. or about 5° C. to about 10° C. and aged a sufficient amount of time before isolation of the crystals.

The cooled mixture is aged for a sufficient amount of time before isolation. The length of aging before isolation may be varied without a significant impact on the yield. In one embodiment, the mixture is cooled at least about 15 minutes. In another embodiment, the mixture is aged for at least about 30 minutes or at least about 1 hour before isolation. In another embodiment, the mixture is aged for at least about 2 hours, at least about 3 hours, at least about 4 hours, at least about 5 hours, or longer. In other embodiments, the mixture may be aged at least about 10 hours, at least about 15 hours, at least about 20 hours or at least about 24 hours, or longer.

In another embodiment of the invention, the crystals may be collected by filtration or centrifugation and optionally washed to remove residual ethanol. Drying, if desired may also be carried out. Appropriate drying conditions should be chosen to avoid melting of compound of formula (Ia). For example, extreme heat should be avoided during drying conditions.

The invention further relates to enantiomerically pure (S)-afoxolaner being in a crystalline form. The crystalline form may be more stable, easier to handle and store, and easier to purify and easier to synthesize in a reproducible manner.

In one aspect, pharmaceutical compositions are provided comprising compound of formula (Ia), for example polymorph Form I, or polymorph Form II, or a mixture thereof, and a pharmaceutically acceptable carrier or diluent. For example, in one embodiment a pharmaceutical composition is provided comprising polymorph Form I, and a pharmaceutically acceptable carrier or diluent. In another embodiment, the invention provides a pharmaceutical composition comprising polymorph Form II and a pharmaceutically acceptable carrier or diluent. In yet another embodiment, the invention provides a pharmaceutical composition comprising a mixture of polymorph Form I and polymorph Form II and a pharmaceutically acceptable carrier or diluent.

When the compounds of the present invention are administered as pharmaceuticals to animals, e.g., mammals, they can be given per se or as a pharmaceutical composition containing, for example, 0.1% to 99.9% (w/w) (more preferably, 0.5 to 90%) of active ingredient in combination with a pharmaceutically acceptable carrier. In other embodiments, the pharmaceutical compositions comprises about 0.5% to about 50% (w/w), about 0.5% to about 25% (w/w) of the compound of formula (Ia) as Form I, Form II or a mixture thereof. In other embodiments, the pharmaceutical compositions comprise about 0.5% to about 15% (w/w) or about 0.5% to about 10% (w/w) as Form I, Form II or a mixture thereof. In yet another embodiment, the pharmaceutical compositions comprise about 0.1% to about 5% (w/w) or about 0.1% to about 2.5% (w/w) of the compound of formula (Ia) as Form I, Form II or a mixture thereof.

In another aspect of the invention is compositions comprising mixtures of two or more forms or mixtures of crystalline (e.g. Form I and Form II) and non-crystalline compound of formula (Ia) that may possess particular advantages in extended release formulations. Thus, the invention also relates to mixtures of such crystalline compound of formula (Ia) products.

In another aspect of the invention, the crystalline compound of formula (Ia) comprises a mixture of crystalline (e.g. Form I and Form II) and non-crystalline forms. For example, the % crystallinity of the compound of formula (Ia) can be at least about 10%, preferably at least about 20% (by weight) of the total compound of formula (Ia), preferably in an amount of at least about 30%, at least about 40%, at least about 50%, at least about 60% (by weight) of the total compound of formula (Ia).

In one embodiment the % crystallinity of compound of formula (Ia) is present in a composition in an amount between about 10% and 70%, preferably between about 30% and 50% (by weight), of the total compound of formula (Ia).

The crystal forms described herein can be combined with a pharmaceutically acceptable carrier according to conventional pharmaceutical compounding techniques. Furthermore, the carrier may take a wide variety of forms depending on the form of the preparation desired for administration, e.g. oral (e.g. tablets, capsules or soft chews) or parenteral (including intravenous injections or infusions). In preparing compositions for oral dosage form any of the usual pharmaceutical media may be employed. Usual pharmaceutical media include, for example, water, glycols, oils, alcohols, flavoring agents, preservatives, coloring agents, surfactants, solvents, binders, humectants, and the like in the case of oral liquid preparations (such as for example, suspensions, solutions, emulsions and elixirs); aerosols; or carriers such as starches (e.g. corn starch), sugars, microcrystalline cellulose, diluents, granulating agents, lubricants, binders (e.g. povidone, solid polyethylene glycol, and the like), disintegrating agents and the like, in the case of oral solid preparations (such as for example, powders, capsules, tablets and soft chews).

Wetting agents, emulsifiers, surfactants and lubricants, such as sodium lauryl sulfate, and magnesium stearate, as well as coloring agents, release agents, coating agents, sweetening, flavoring and perfuming agents, preservatives and antioxidants also can be present in the compositions. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, tocopherols, and the like; and metal chelating agents, such as citric acid, ethylenediamine tetraacetic acid (EDTA), sorbitol, tartaric acid, phosphoric acid, and the like.

Examples of suitable surfactants for pharmaceutical compositions for include glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-ca-tocopherol polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides (GELUCIRE®), PEG 300 caprylic/capric glycerides (Soffigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like. Surfactants may be present in the composition at concentrations of about 0.1% to about 10% (w/w), about 1% to about 10% (w/w) or about 5% to about 10% (w/w). More typically, surfactants may be present at concentrations of about 0.1% to about 5% (w/w) or about 1 to about 5% (w/w).

Fillers that may be used in oral formulations include, but are not limited to, corn starch, pre-gelatinized corn starch, soy protein fines, corn cob, and corn gluten meal, and the like, or a combination thereof. Fillers are typically present in the compositions at a concentration of about 5% to about 80% (w/w), about 10% to about 70% (w/w), about 10% to about 60%, about 100% to about 50% (w/w), or about 10% to about 40% (w/w). More typically, the fillers may be present at concentrations of about 30% to about 70%, about 30% to about 60%, about 30% to about 50% or about 35% to about 55%.

Binders that may be used in compositions of the invention for oral administration include, but are not limited to, polyvinylpyrrolidone (e.g. Povidone), cross-linked polyvinylpyrrolidone (Crospovidone), polyethylene glycols of various grades including PEG 3350, PEG 4000, PEG 6000, PEG 8000 and even PEG 20,000, and the like; co-polymers of vinylpyrrolidone and vinyl acetate (e.g. Copovidone) such as the product sold by BASF by the tradename Kollidon® VA 64 and the like; starch such as potato starch, tapioca starch or corn starch; molasses, corn syrup, honey, maple syrup and sugars of various types; or a combination of two or more binders. In one embodiment, the composition comprises the binders Povidone K30 LP and PEG 3350 or PEG 4000, or a combination thereof. Binders are typically present in the compositions at a concentration of about 1% to about 30% (w/w). More typically, the compositions will include binders at a concentration of about 1% to about 20% (w/w), about 1 to about 15% (w/w), about 1% to about 10% (w/w), about 5% to about 15% (w/w) or about 5% to about 10% (w/w).

Solvents that may be used in the compositions of the invention include, but are not limited to, various grades of liquid polyethylene glycol (PEG) including PEG 200, PEG 300, PEG 400 and PEG 540; propylene carbonate; propylene glycol; triglycerides including, but not limited to caprylic/capric triglyceride, caprylic/capric/linoleic triglyceride (e.g. MIGLYOL® 810 and 812, caprylic/capric/succinic triglyceride, propylene glycol dicaprylate/dicaprate, and the like; water, sorbitol solution, glycerol caprylate/caprate and polyglycolized glycerides (GELUCIRE®), 2-pyrrolidone, N-methylpyrrolidone (NMP), dimethylacetamide, or a combination thereof.

Solvents may be included in the compositions in concentrations of about 1 to about 50% (w/w). In other embodiments, the concentration of the solvents will be from about 1 to about 40% (w/w), about 1 to about 30% (w/w) or about 1 to about 20% (w/w). More typically, the solvents will be in the compositions at concentrations of about 5% to about 20% (w/w) or about 5% to about 15% (w/w).

Humectants that may be used in the compositions include, but are not limited to, glycerol (also referred to herein as glycerin), propylene glycol, cetyl alcohol and glycerol monostearate, and the like. Polyethylene glycols of various grades may also be used as humectants. Humectants may typically present in the compositions at a concentration of about 1% to about 25% (w/w). Typically, the concentration of the humectant in the composition of the invention will be 1% to about 20% (w/w), about 1% to about 15% (w/w) or about 5% to about 15% (w/w). More typically, the compositions of the invention will contain about 1% to about 10% (w/w) humectant.

Pharmaceutical compositions comprising a crystal form of the compound of formula (Ia) (e.g. Form I and/or Form II) may be formulated to have any concentration desired, preferably an amount which is therapeutically effective and would not cause one or more unwanted side effects.

Because of their ease of administration, tablets, soft chew dosage forms and capsules may represent the most advantageous oral dosage unit form, in which case solid pharmaceutical carriers may be employed. If desired, tablets and soft chew dosage forms may be coated by techniques known to those in the art.

In certain embodiments, the pharmaceutical composition comprises varying amounts of a crystal form of the compound of formula (Ia), based on the total weight of compound of formula (Ia) in the composition. In one embodiment, the pharmaceutical composition comprises less than 1% by weight of the crystal form of the polymorph Form I of compound of formula (Ia). In another embodiment, the pharmaceutical composition comprises less than 1% by weight of the crystal form of the polymorph Form I of compound of formula (Ia). In another embodiment, the pharmaceutical composition comprises less than 10% by weight of the crystal form of the polymorph Form I of compound of formula (Ia). In another embodiment, the pharmaceutical composition comprises less than 25% by weight of the polymorph Form I of the compound of formula (Ia).

In another embodiment, the pharmaceutical composition comprises less than 50% by weight of the polymorph Form I of the compound of formula (Ia). In another embodiment, the pharmaceutical composition comprises less than 99% by weight of the polymorph Form I of the compound of formula (Ia).

In other embodiments, the pharmaceutical compositions of the invention comprise at least about 30% (w/w), at least about 50% (w/w) or at least about 70% (w/w) of a compound of formula (Ia) as polymorph Form I. In another embodiment, the pharmaceutical compositions of the invention comprise at least about 80% (w/w), at least about 90% (w/w) or at least about 95% (w/w) of the compound of formula (Ia) as polymorph Form I. In yet another embodiment, the compositions of the invention comprise at least about 99% (w/w) of the compound of formula (Ia) as Form I.

In another embodiment, the pharmaceutical composition comprises less than 1% by weight of the crystal form of the polymorph Form II of compound of formula (Ia). In another embodiment, the pharmaceutical composition comprises less than 1% by weight of the crystal form of the polymorph Form II of compound of formula (Ia). In another embodiment, the pharmaceutical composition comprises less than 10% by weight of the crystal form of the polymorph Form II of compound of formula (Ia). In another embodiment, the pharmaceutical composition comprises less than 25% by weight of the polymorph Form II of the compound of formula (Ia).

In another embodiment, the pharmaceutical composition comprises less than 50% by weight of the polymorph Form II of the compound of formula (Ia). In another embodiment, the pharmaceutical composition comprises less than 99% by weight of the polymorph Form II of the compound of formula (Ia).

In other embodiments, the pharmaceutical compositions of the invention comprise at least about 30% (w/w), at least about 50% (w/w) or at least about 70% (w/w) of a compound of formula (Ia) as polymorph Form II. In another embodiment, the pharmaceutical compositions of the invention comprise at least about 80% (w/w), at least about 90% (w/w) or at least about 95% (w/w) of the compound of formula (Ia) as polymorph Form II. In yet another embodiment, the compositions of the invention comprise at least about 99% (w/w) of the compound of formula (Ia) as Form II.

Pharmaceutical compositions include those suitable for oral, sublingual, nasal, rectal, vaginal, topical (e.g. spot-ons or pour-ons), buccal and parenteral (including subcutaneous, intramuscular, and intravenous) administration, although the most suitable route will depend on the nature and severity of the condition being treated. The compositions may be conveniently presented in unit dosage form, and prepared by any of the methods well known in the art of pharmacy. In certain embodiments, the pharmaceutical composition is formulated for oral administration in the form of a pill, capsule, soft chewable dosage forms, lozenge or tablet. In other embodiments, the pharmaceutical composition is in the form of a suspension.

Pharmaceutical compositions comprising a specific crystal form can be identified by comparison of the compositions' X-ray powder diffraction patterns to an X-ray powder diffraction pattern of the pure specific crystal form. It will be appreciated that pharmaceutical compositions comprising a specific crystal form may exhibit non-identical X-ray powder diffraction patterns as compared to an X-ray powder diffraction pattern of the pure specific polymorphic crystal form.

Also provided herein are crystal forms that are bioequivalent to any one or more of polymorphic Forms I and II of (S)-afoxolaner described herein. In certain embodiments, bioequivalence between two crystal forms refers to crystal forms having substantially similar bioavailability, substantially similar efficacy, substantially similar safety profiles, or a combination thereof.

In yet other embodiments, bioequivalence refers to crystal forms that exhibit substantially similar pharmacokinetic profiles or therapeutic effects. Bioequivalence may be demonstrated through several in vivo and in vitro methods. These methods may include, for example, pharmacokinetic, pharmacodynamic, clinical and in vitro studies. In some embodiments, bioequivalence can be demonstrated using any suitable pharmacokinetic measures or combination of pharmacokinetic measures known in the art, including loading dose, steady-state dose, initial or steady-state concentration of drug, biological half-life, elimination rate, area under the curve (AUC), clearance, the peak blood or plasma concentration (C), time to peak concentration (T), bioavailability and potency. In some embodiments, bioequivalence is achieved with similar dosing amounts. In alternative embodiments, bioequivalence is achieved with different dosing amounts.

In view of the pharmaceutical value of crystalline (S)-afoxolaner, it has been important to be able to obtain it by an effective synthesis process that is readily scalable and that results in crystalline (S)-afoxolaner in a good yield and with excellent enantiomeric purity and chemical purity.

The Applicant has now developed a new synthesis process that results, in a reproducible manner and without the need for laborious purification, in crystalline (S)-afoxolaner of a purity compatible with its use as a pharmaceutical active ingredient.

The examples are presented to further illustrate and explain the present invention and should not be taken as limiting in any regard. Unless otherwise indicated in the examples and elsewhere in the specification and claims, all parts and percentages are by weight. Temperatures are in degrees Centigrade.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is noted that the invention does not intend to encompass within the scope of the invention any previously disclosed composition, product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

EXAMPLES

Example 1: Synthesis of Racemic Afoxolaner and (S)-Afoxolaner

Racemic afoxolaner can be obtained by a process such as that disclosed by U.S. Pat. No. 8,410,153, which is incorporated herein by reference in its entirety. Enantiomerically enriched afoxolaner enriched in the (S)-enantiomer can be obtained by a process such as that disclosed by U.S. Application No. 62/319,207, which is the priority document for U.S. Ser. No. 15/480,316 published as US 2017/0311601 A1, all incorporated herein by reference in its entirety.

Example 2—Synthesis of Crystalline Toluene Solvate of (S)-Afoxolaner (a) Synthesis of (S)-Afoxolaner

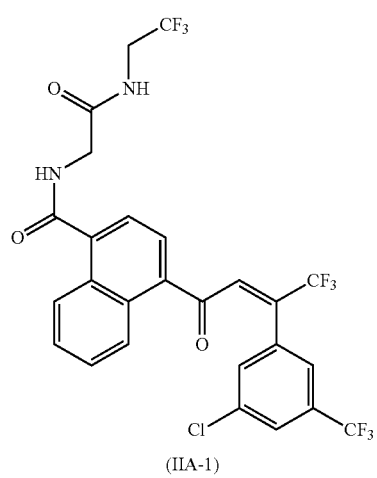

(IIA-1)

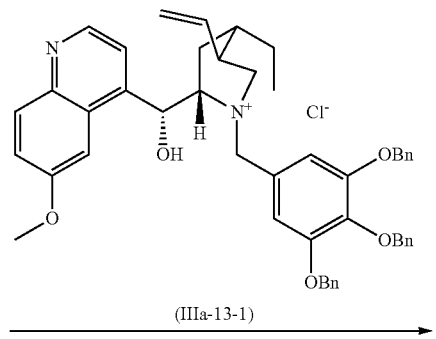

(IIIa-13-1)

-continued

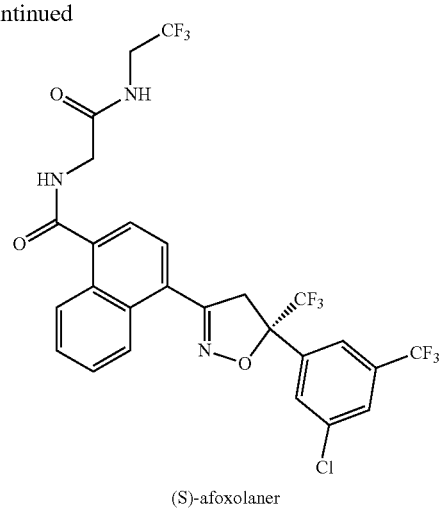

(S)-afoxolaner 1. 1 kilogram of compound (IIA-I) (1 eq.) and 9 volumes of dichloromethane (DCM) are charged to a reactor and stirred to dissolve the compound.
2. The mixture is cooled to about 0° C. and 50 grams (5% by wt. of compound (IIA-I)) of the chiral phase transfer catalyst (IIIa-13-1) and 1 liter of DCM are charged and the resulting mixture is cooled to about −13° C.
3. A solution of 19% (w/w) hydroxylamine sulfate (294 g, 1.1 eq.) (made with 294 grams of (NH$_2$OH)H$_2$SO$_4$ and 141 grams of NaCl in 1112 mL of water) and 4.4 equivalents of NaOH as a 17.6% (w/w) solution (286 grams NaOH and 158 grams of NaCl in 1180 mL water) are charged to the reaction mixture simultaneously.
4. The resulting reaction mixture was vigorously mixed about 20 hours at about −13° C. and then checked for reaction conversion by HPLC (target ≤0.5% by area);
5. After completion of the reaction, water (3 vol.) was added at about 0° C. Then, a solution of 709 g of KH$_2$PO$_4$ in 4.2 liters of water are added to the mixture to adjust the pH (target 7-8) and the resulting mixture is stirred at about 20° C. for 30 minutes.
6. The layers are allowed to settle, the aqueous layer is removed and the organic layer is washed with 3 liters of water twice to afford (S)-afoxolaner in the organic layer.

b) Crystallization of Toluene Solvate

1. After the extraction/washing step in Example 2(a)(6) above, the dichloromethane is removed by distillation under vacuum to about 1-2 volumes and toluene (about 5-10 volumes) is added.
2. The volume is adjusted by further distillation under vacuum and/or addition of more toluene to about 5-6 volumes. The mixture is distilled further while maintaining the volume to largely remove the dichloromethane reaction solvent.
3. The mixture is then cooled to about 10° C. and seeded with afoxolaner (racemic compound) and stirred at the same temperature for at least 2 hours;
4. The mixture is heated to about 55-65° C., and aged (in one embodiment for at least 17 hours) and then the solid racemate is filtered off. The filtered solid is washed with toluene;
5. The combined filtrate and wash is adjusted to a volume of about 5-6 volumes by distillation under vacuum and/or toluene addition;
6. The resulting mixture is cooled to about 10° C. and aged for at least 5 hours then filtered. The cake is washed with toluene.
7. The cake is dried at 50° C. under vacuum to obtain a crystalline toluene solvate of (S)-Afoxolaner, as rod like crystals.

Example 3: Formation of Crystalline Form I of (S)-Afoxolaner from Ethanol/Cyclohexane In a 25 L jacketed vessel at 20° C. was added the following materials:

| | |
|---|---|
| (S)-afoxolaner toluene solvate (e.e. 96%) | 591 g |
| EtOH (Ethanol) | 709 ml |
| Cyclohexane | 1773 ml |

After addition of the materials, the reaction mixture was heated to about 60° C. at a rate of 20° C./h and stirred. The rate of heating is not essential and is dependent on the equipment used. After about one hour, an additional 6.4 L of cyclohexane was added and the stirring speed adjusted to 100 rpm (0.04 W.L-1) and cool to 55° C. The mixture may be seeded at this stage to aid with crystal formation. The mixture then underwent the following sequence of steps twice:
  Cooled to 30° C. (−10° C./h)
  Stirred at 30° C. for 30 min
  The stirring power was increased to 0.13 W.L-1
  Heated to 60° C. (15° C./h)
  Stir at 60° C. for 1 h
After the second sequence was completed, the mixture was cooled mixture to 10° C. at a rate of −5° C./h and stirred for 5 h minimum at 10° C. The suspension was then filtered at 10° C. and washed twice at 10° C. with cyclohexane (i.e. 2×1.2 L). The filtered crystals were then dried under vacuum (50 mbar) at 50° C. for 20 h to afford 453.7 g of non-solvated crystalline (S)-afoxolaner with a chemical purity greater than 94%, (e.e. ≥96%). Thermographic analysis (TGA) showed no weight loss to indicate the presence of a solvate crystalline form. The non-solvated crystalline (S)-afoxolaner was determined to be Form I by XRPD.

Example 4: Formation of Crystalline Form II of (S)-Afoxolaner from Ethanol/Cyclohexane Using a process similar to Example 3 but using 100% optically pure (S)-afoxolaner toluene solvate and 15/85% v/v of ethanol to cyclohexane as the crystallization solvent, afforded Form II of (S)-afoxolaner. Thermographic analysis (TGA) showed no weight loss to indicate the presence of a solvate crystalline form. The non-solvated crystalline (S)-afoxolaner was determined to be Form II by XRPD.

X-Ray Powder Diffraction (XRPD) Analysis of (S)-Afoxolaner Forms I and II

TABLE 1 summarizes the peaks in the X-ray Diffraction Patterns of (S)-afoxolaner Forms I and II, measured using the following apparatus and parameters:

Apparatus: Bruker D8 Advance diffractometer
Source CuKa1 1=1.5406 Å; CuKa2 12=1.54436 Å
Generator: 40 kV-30 mA
Detector: lynx Eye.
PMMA sample holder
Phi spinner:
Rotation speed: 30 rpm
Angle range: 2° to 40° in theta-theta
Variable divergence slit: 12 mm (V12)
Step size: 0.02°
Step time 10.6 s Form I shows the most prominent peaks at 2θ=10.03°, 10.48°, 13.16°, 15.42°, 15.80°, 16.07°, 17.65°, 20.16°, 22.15°, 23.68°, 26.52°, and 28.13°. By contrast, Form II shows the most prominent peaks at 2θ=5.99°, 12.99°, 15.80°, 18.71°, 19.33°, 20.24°, 21.65°, 22.17°, 26.11°, 29°.

TABLE 1

| | Form I XRPD peak list | | | | Form II XRPD peak list | | | |
|---|---|---|---|---|---|---|---|---|
| Peak No | Angle (2θ) | D value (Å) | Intensity (I) | I/Imax (%) | Peak No | Angle (2θ) | D value (Å) | Intensity (I) | I/Imax (%) |
| 1 | 5.02 | 17.576 | 187 | 2.9 | 1 | 5.99 | 14.7493 | 3182 | 43.7 |
| 2 | 5.87 | 15.045 | 513 | 8.0 | 2 | 10.08 | 8.7712 | 995 | 13.7 |
| 3 | 6.07 | 14.560 | 656 | 10.3 | 3 | 10.51 | 8.4084 | 1717 | 23.6 |
| 4 | 10.03 | 8.810 | 1725 | 27.0 | 4 | 11.97 | 7.3855 | 1513 | 20.8 |
| 5 | 10.48 | 8.437 | 1776 | 27.8 | 5 | 12.99 | 6.8089 | 4067 | 55.8 |
| 6 | 11.74 | 7.532 | 348 | 5.4 | 6 | 13.51 | 6.5508 | 506 | 6.9 |
| 7 | 12.16 | 7.273 | 790 | 12.4 | 7 | 15.80 | 5.6046 | 7286 | 100 |
| 8 | 13.16 | 6.723 | 1635 | 25.6 | 8 | 16.29 | 5.4384 | 693 | 9.5 |
| 9 | 13.57 | 6.520 | 363 | 5.7 | 9 | 17.63 | 5.0263 | 1338 | 18.4 |
| 10 | 15.42 | 5.742 | 1003 | 15.7 | 10 | 18.00 | 4.9236 | 1260 | 17.3 |
| 11 | 15.80 | 5.604 | 3492 | 54.6 | 11 | 18.44 | 4.8071 | 884 | 12.1 |
| 12 | 16.07 | 5.511 | 2125 | 33.2 | 12 | 18.71 | 4.7400 | 1618 | 22.2 |
| 13 | 17.65 | 5.021 | 3249 | 50.8 | 13 | 19.33 | 4.5872 | 2761 | 37.9 |
| 14 | 18.29 | 4.847 | 643 | 10.1 | 14 | 20.24 | 4.3843 | 4113 | 56.5 |
| 15 | 19.00 | 4.668 | 1558 | 24.4 | 15 | 20.67 | 4.2943 | 2805 | 38.5 |
| 16 | 19.44 | 4.563 | 1635 | 25.6 | 16 | 21.09 | 4.2099 | 1317 | 18.1 |
| 17 | 20.16 | 4.400 | 6394 | 100 | 17 | 21.65 | 4.1013 | 5788 | 79.4 |
| 18 | 20.90 | 4.246 | 1830 | 28.6 | 18 | 22.17 | 4.0068 | 6022 | 82.7 |
| 19 | 21.50 | 4.129 | 1010 | 15.8 | 19 | 23.11 | 3.8462 | 1007 | 13.8 |
| 20 | 22.15 | 4.010 | 4327 | 67.7 | 20 | 23.58 | 3.7702 | 2753 | 37.8 |
| 21 | 23.04 | 3.857 | 991 | 15.5 | 21 | 24.07 | 3.6944 | 1037 | 14.2 |
| 22 | 23.68 | 3.754 | 2089 | 32.7 | 22 | 24.62 | 3.6137 | 2338 | 32.1 |
| 23 | 24.66 | 3.608 | 1298 | 20.3 | 23 | 25.19 | 3.5321 | 1035 | 14.2 |
| 24 | 25.04 | 3.553 | 2004 | 31.3 | 24 | 25.60 | 3.4766 | 857 | 11.8 |
| 25 | 25.34 | 3.511 | 1379 | 21.6 | 25 | 26.11 | 3.4098 | 5723 | 78.5 |
| 26 | 26.09 | 3.412 | 1195 | 18.7 | 26 | 26.93 | 3.3080 | 915 | 12.6 |
| 27 | 26.33 | 3.382 | 1489 | 23.3 | 27 | 27.19 | 3.2776 | 1137 | 15.6 |
| 28 | 26.52 | 3.358 | 1774 | 27.7 | 28 | 27.67 | 3.2218 | 734 | 10.1 |
| 29 | 26.92 | 3.309 | 1162 | 18.2 | 29 | 28.12 | 3.1705 | 1466 | 20.1 |
| 30 | 27.38 | 3.254 | 732 | 11.4 | 30 | 29.00 | 3.0761 | 3663 | 50.3 |
| 31 | 28.13 | 3.169 | 1596 | 25.0 | 31 | 29.57 | 3.0187 | 1271 | 17.4 |
| 32 | 28.88 | 3.089 | 781 | 12.2 | 32 | 30.22 | 2.9555 | 2397 | 32.9 |
| 33 | 29.55 | 3.020 | 1305 | 20.4 | 33 | 30.67 | 2.9130 | 872 | 12 |
| 34 | 30.77 | 2.904 | 1210 | 18.9 | 34 | 31.24 | 2.8611 | 790 | 10.8 |

Differential Scanning Calorimetry Thrmogram Analysis of (S)-afoxolaner Forms I and II Form I and Form II were measured using the following apparatus and parameters:

Apparatus: PerkinElmer Diamond DSC
Atmosphere: Nitrogen 20 ml/min
Pan: 50 μl Aluminium pan
Lid: perforated Aluminium lid with 100 μm hole
Rate: 5° C./min Form I: differential scanning calorimetry (DSC) thermogram having a peak at a temperature of about 146° C., and an onset at about 143° C.

Form II: differential scanning calorimetry (DSC) thermogram having a peak at a temperature of about 149° C., and an onset at about 146° C.

Example 5: Formation of the Crystalline Form I of (S)-Afoxolaner from Ethyl Acetate Following the procedure of Example 3, but using Ethyl Acetate rather than EtOH/Cyclohexane mixture and after the second sequence was completed, the mixture was cooled to 4° C. at a rate of −5° C./h and stirred for 72 h at 4° C., the crystalline Form I of (S)-afoxolaner was isolated.

Example 6: Formation of the Crystalline Form I of (S)-Afoxolaner from Acetonitrile Following the procedure of Example 3, but using Acetonitrile rather than EtOH/Cyclohexane mixture, and after the second sequence was completed, the mixture was cooled mixture to 4° C. at a rate of −5° C./h and stirred for 72 h at 4° C., the crystalline Form I of (S)-afoxolaner was isolated.

What is claimed is:

1. A pharmaceutical composition for oral administration comprising an effective amount of a crystalline compound of formula (Ia), designated as Form I,

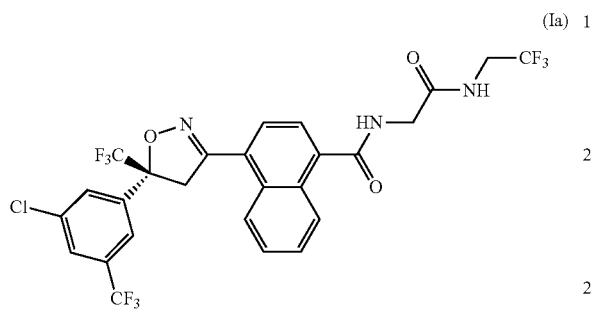

(Ia)

wherein said crystalline compound of formula (Ia) is characterized by having an x-ray powder diffraction pattern comprising three, four, five, six, seven or more peaks selected from the group consisting of: 10.03°, 10.48°, 13.16°, 15.42°, 15.80°, 16.07°, 17.65°, 20.16°, 22.15°, 23.68°, 26.52°, and 28.13° 2θ±0.2 as determined on a diffractometer using Cu-Kα radiation; and a pharmaceutically acceptable carrier.

2. The pharmaceutical composition of claim 1, wherein the composition is in the form of a soft chew.

3. The pharmaceutical composition of claim 1, wherein the composition is in the form of a tablet.

4. The pharmaceutical composition of claim 1, wherein the crystalline compound of formula (Ia) exhibits an x-ray powder diffraction pattern comprising three or more peaks selected from the group consisting of: 10.03°, 10.48°, 13.16°, 20.16°, and 22.15° 2θ±0.2 as determined on a diffractometer using Cu-Kα radiation.

5. The pharmaceutical composition of claim 1, wherein the crystalline compound of formula (Ia) exhibits an x-ray powder diffraction pattern substantially similar to FIG. 1.

6. The pharmaceutical composition of claim 1, wherein the crystalline compound of formula (Ia) exhibits a differential scanning calorimetry (DSC) thermogram having an peak at a temperature of about 146° C., and an onset at about 143° C., measured with the heating rate of 5° C./min.

7. The pharmaceutical composition of claim 1, wherein the crystalline compound of formula (Ia) exhibits a differential scanning calorimetry (DSC) thermogram having a heat of fusion of about 61.7 J/g.

8. The pharmaceutical composition of claim 1, wherein the crystalline compound of formula (Ia) exhibits a differential scanning calorimetry thermogram substantially similar to FIG. 2.

9. The pharmaceutical composition of claim 1, wherein the composition further comprises a crystalline compound of formula (Ia) designated as Form II and/or an amorphous form of the compound of formula (Ia); wherein the crystalline compound of formula (Ia) designated Form II is characterized by having an X-ray powder diffraction pattern comprising three, four, five, six, seven or more peaks selected from the group consisting of: 5.99°, 12.99°, 15.80°, 18.71°, 19.33°, 20.24°, 21.65°, 22.17°, 26.11° and 29.00° 2θ±0.2 as determined on a diffractometer using Cu-Kα radiation.

10. The pharmaceutical composition of claim 9, wherein the composition comprises at least 70% by weight of the crystalline compound of formula (Ia) Form I according to claim 1, based on the total weight of compound of formula (Ia) in the composition.

11. The pharmaceutical composition of claim 9, wherein the composition comprises at least 90% by weight of the crystalline compound of formula (Ia) Form I according to claim 1, based on the total weight of compound of formula (Ia) in the composition.

12. The pharmaceutical composition of claim 2, wherein the pharmaceutically carrier comprises a surfactant, a filler and a binder.

13. The pharmaceutical composition of claim 12, wherein the pharmaceutically acceptable carrier further comprises a solvent.

14. The pharmaceutical composition of claim 12, wherein the pharmaceutically acceptable carrier further comprises a flavoring agent.

15. The pharmaceutical composition of claim 12, wherein the filler comprises corn starch, pre-gelatinized corn starch, soy protein fines, or a combination thereof.

16. The pharmaceutical composition of claim 1, wherein the concentration of the compound of formula (Ia) in the composition is about 0.5% to about 10% (w/w).

17. The pharmaceutical composition of claim 1, wherein the concentration of the compound of formula (Ia) in the composition is about 0.1% to about 5% (w/w).

18. The pharmaceutical composition of claim 9, wherein the concentration of the compound of formula (Ia) in the composition is about 0.5% to about 10% (w/w).

19. The pharmaceutical composition of claim 9, wherein the concentration of the compound of formula (Ia) in the composition is about 0.1% to about 5% (w/w).

20. The pharmaceutical composition of claim 12, wherein the concentration of the compound of formula (Ia) in the composition is about 0.5% to about 10% (w/w).

21. The pharmaceutical composition of claim 12, wherein the concentration of the compound of formula (Ia) in the composition is about 0.1% to about 5% (w/w).

* * * * *